United States Patent
Toth et al.

Patent Number: 6,052,434
Date of Patent: *Apr. 18, 2000

[54] X-RAY TUBE TARGET FOR REDUCED OFF-FOCAL RADIATION

[76] Inventors: Thomas L. Toth; Willi H. Hampel; Stephen W. Gravelle; Wayne F. Block, all of P.O. Box 414, Milwaukee, Wis. 53201

[ * ] Notice: This patent issued on a continued prosecution application filed under 37 CFR 1.53(d), and is subject to the twenty year patent term provisions of 35 U.S.C. 154(a)(2).

[21] Appl. No.: 08/777,369

[22] Filed: Dec. 27, 1996

[51] Int. Cl.[7] ................................................. H01J 35/08
[52] U.S. Cl. .................................... 378/143; 378/144
[58] Field of Search ......................................... 378/143, 144

[56] References Cited

U.S. PATENT DOCUMENTS

| | | | |
|---|---|---|---|
| 3,113,233 | 12/1963 | Kasten, Jr. et al. | 378/144 |
| 4,321,471 | 3/1982 | Holland et al. | 378/207 |
| 4,461,019 | 7/1984 | Lersmacher | 378/144 |
| 4,958,364 | 9/1990 | Guerin et al. | 378/144 |

*Primary Examiner*—Craig E. Church
*Attorney, Agent, or Firm*—B. Joan Haushalter; Christian G. Cabou; Phyllis Y. Price

[57] ABSTRACT

An X-ray tube comprises an anode assembly having an associated anode and a cathode assembly for providing a focused electron beam directed to the anode. An anode target, associated with the anode assembly, accelerates the electron beam and produces X-rays upon electron impact with the anode target. Off-focal radiation tends to be most intensely emitted by the top surface of the target. In conventional X-ray tubes, the off-focal radiation as seen by the detector encompasses almost the entire top surface of the target assembly. In accordance with the present invention, the anode target comprises a cut-out top surface for reducing off-focal radiation, by blocking the off-focal radiation from the top surface from reaching the detector. Blocking the radiation produced at the top surface becomes more important as the ratio of the track area visible at the detector decreases with respect to the top surface area.

10 Claims, 2 Drawing Sheets

X-RAY TUBE TARGET FOR REDUCED OFF-FOCAL RADIATION

TECHNICAL FIELD

The present invention relates to X-ray tubes and more particularly, to an X-ray tube target for reducing off-focal radiation.

BACKGROUND ART

The X-ray tube has become essential in medical diagnostic imaging, medical therapy, and various medical testing and material analysis industries. Typical X-ray tubes are built with a rotating anode structure for the purpose of distributing the heat generated at the focal spot. The anode is rotated by an induction motor comprising a cylindrical rotor built into a cantilevered axle that supports the disc shaped anode target, and an iron stator structure with copper windings that surrounds the elongated neck of the X-ray tube that contains the rotor. The rotor of the rotating anode assembly is driven by the stator which surrounds the rotor of the anode assembly. The X-ray tube cathode provides a focused electron beam which is accelerated across the anode-to-cathode vacuum gap and produces X-rays upon impact with the anode.

One of the factors that tends to degrade X-ray, particularly computerized tomography (CT), images is the production of x-radiation at points in the X-ray tube other than the focal spot. Most of this off-focal radiation is caused by electrons that have scattered from the focal spot to hit other points of the target and the tube. In CT, this off-focal radiation creates image artifacts, particularly near the bone bran interface in head scans, where it can obscure trauma injuries or can appear as false positive medical problems. Current tube designs with software correction algorithms are marginal. New CT products being developed are more sensitive to off focal radiation since they use wider X-ray beams to accommodate multi-slice detectors and shorter geometries. Of particular importance is the need for a uniform X-ray beam in the Z-axis on the detector. Off-focal radiation creates an additional non-uniformity that requires wider collimation and, hence, increased patient X-ray dose in order to avoid the nonuniformity. The increased nonuniformity also increases the need for sophisticated software corrections and collimation apparatus.

It would be desirable, then, to have an X-ray tube structure which reduces off-focal radiation.

SUMMARY OF THE INVENTION

The present invention reduces off-focal radiation by a significant percent, compared to a standard anode tube, by providing for a cut-out in the top of the anode.

In accordance with one aspect of the present invention, an X-ray tube comprises an anode assembly having an associated anode and a cathode assembly for providing a focused electron beam directed to the anode. An anode target, also associated with the anode assembly, accelerates the electron beam and produces X-rays upon electron impact with the anode target. The anode target comprises a cut-out top surface for reducing off-focal radiation.

Accordingly, it is an object of the present invention to reduce off-focal radiation by a significant amount, as compared to a standard anode tube. An additional advantage is that the reduced variation in off-focal radiation intensity with detector Z position eliminates the need for multiple correction kernels on multislice CT systems. Additionally, the reduced off-focal radiation improves the flatness of the X-ray beam umbra region that is required for multislice systems, and thereby minimizes excess patient dose.

Other objects and advantages of the invention will be apparent from the following description, the accompanying drawings and the appended claims.

DETAILED DESCRIPTION OF THE PREFERRED EMBODIMENTS

The present invention relates to rotating anode X-ray tubes which employ a rotating anode assembly and a cathode assembly. The purpose of this invention is to reduce the off-focal radiation of X-ray tubes.

Figure 1:
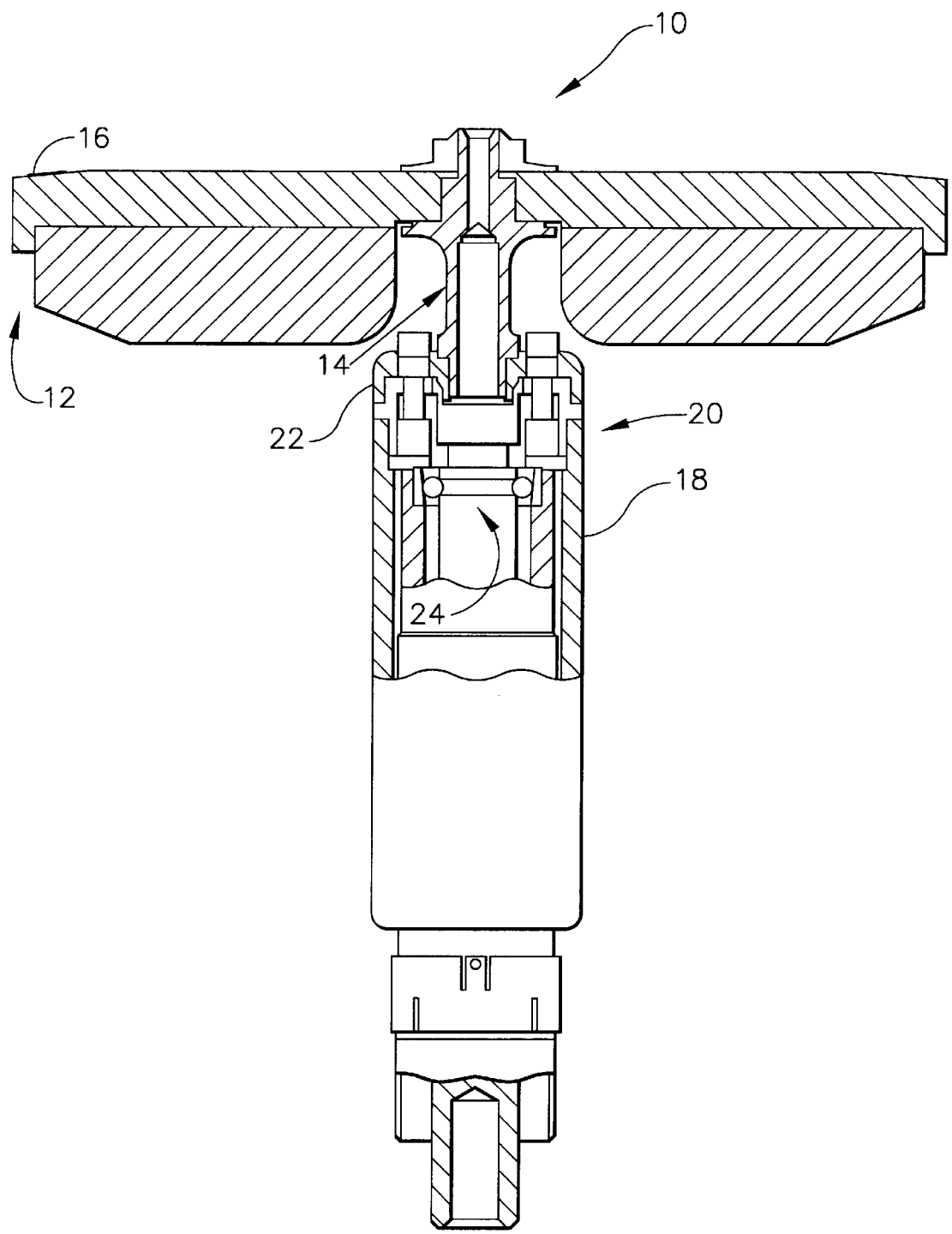
FIG. 1 is a prior art cross-sectional illustration of a typical X-ray tube anode.

Referring now to the drawings, FIG. 1 illustrates a typical prior art X-ray tube anode 10. The X-ray tube anode 10 is typically built with a rotating target assembly 12, having an associated stem 14, for the purpose of distributing the heat generated at focal spot 16. The anode assembly 10 comprises target assembly 12 and rotor 18, also at anodic potential. A typical X-ray tube further comprises an X-ray tube cathode assembly (not shown) for providing a focused electron beam which is accelerated across an anode-to-cathode vacuum gap, producing X-rays upon impact with the target.

Continuing with FIG. 1, the anode assembly 10 is rotated by an induction motor comprising the cylindrical rotor 18 built around a cantilevered axle 20. The cantilevered axle 20 supports the disc shaped target assembly 12 connected via stud 14 and hub 22 to rotor 18 and bearing assembly 24, which contains bearings facilitating rotation. The rotor 18 of the rotating anode assembly 10, driven by a stator of the induction motor, is at anodic potential.

Figure 2A:
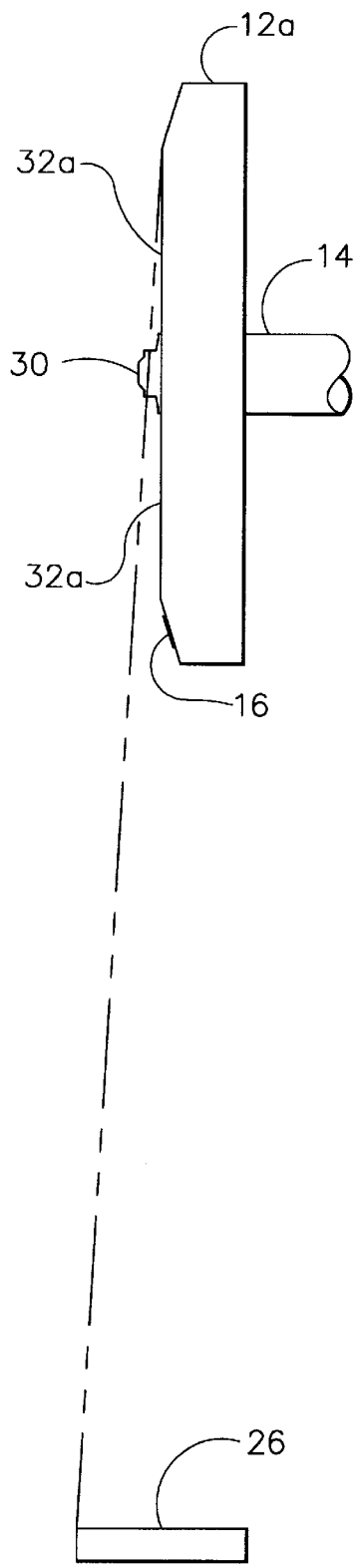
FIG. 2A is a side view illustrating a conventional target assembly portion of the X-ray tube anode of FIG. 1.

Referring now to FIG. 2A, off-focal radiation tends to be most intensely emitted by top surface 32a of target assembly 12a. In conventional X-ray tubes, then, the off-focal radiation, as seen by detector 26, encompasses almost the entire top surface of target assembly 12a. The present invention proposes blocking the off-focal radiation from the top 32a of the target 12a from reaching the detector 26. Blocking the radiation produced at the top surface 32a becomes more important as the ratio of the track area visible at the detector decreases with respect to the top surface area 32a.

Figure 2B:
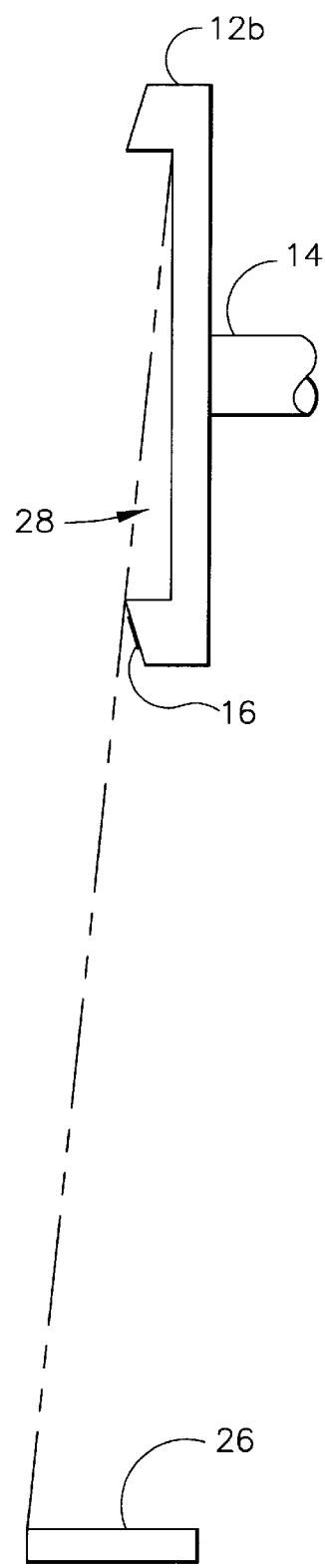
FIG. 2B is a side view of the target assembly for use with the X-ray tube anode of FIG. 1, in accordance with the present invention.

Referring to FIG. 2B, there is illustrated a target 12b design for reducing the off-focal radiation experienced in a standard anode structure, such as is illustrated in FIG. 2A. The top surface comprises a cut-out depth 28 for eliminating line of sight of the top surface of the target 12b from the detector 26, so that the detector does not receive the off-focal radiation emitted from this surface. As seen in the figures, nut 30 of target assembly 12A has also been removed from the target assembly 12b so that the target cut 28 effectively hides the entire top surface for the anode assembly.

In a preferred embodiment of the present invention, the cut-out depth 28 is the minimum depth sufficient to hide the line of sight of the top surface of the target 12b from the detector 26. The minimum depth may be approximately 2.3 mm for some systems, but less or more for other systems, depending on the system configuration. Although a cut-out depth less than the minimum still provides partial reduction in the off-focal radiation received by the detector, it is not as effective at eliminating the off-focal radiation. Conversely, although a cut-out depth greater than the minimum is just as effective at eliminating the off-focal radiation as the minimum depth, strength and heat capacity of the device can be compromised by the greater depth. Hence, the cut-out depth is calculated to hide the surface at the edge of the detector, without cutting out so much that the heat capacity of the anode is adversely affected.

Although the target cut 28 could conceivably have a variety of contours, the squared cut-out illustrated in FIG. 2B is easier to inspect and machine than, for example, a concave surface. Typically, the cut-out is done at the final target processing stage, before being sent for anode assembly.

The present invention provides the advantage of reducing off-focal radiation, since radiation emitted from the anode top surface is blocked from reaching the detector. The present invention provides a more uniform X-ray beam and hence a lower partial dose, as well as the additional advantage of eliminating the off-focal radiation intensity dependence with Z axis position on the detector.

The invention has been described in detail with particular reference to certain preferred embodiments thereof, but it will be understood that modifications and variations can be effected within the spirit and scope of the invention. For example, the present invention may incorporate the utilization of low atomic number materials for the top surface of the target, such as titanium, graphite, ceramics, etc.

We claim:

1. A method for modifying an anode target of an X-ray tube to reduce off-focal radiation produced by the anode target and seen by an associated detector situated along a line of sight of a top surface of the anode target, the method comprising the steps of:

providing an anode target, the top surface of the anode target capable of emitting off-focal radiation, the off-focal radiation detectable by the detector; and modifying the anode target by removing a section of the top surface to create a cut-out depth in the top surface, whereby the cut-out depth blocks the off-focal radiation from the anode target top surface from reaching the detector.

2. A method as claimed in claim 1 wherein the step of modifying the anode target by removing a section of the top surface further comprises the step of forming a cut-out depth in the top surface, the cut-out depth having squared edges.

3. A method as claimed in claim 1 further comprising the step of notching the existing top surface of the anode target to form the cut-out depth.

4. A method as claimed in claim 1 wherein the step of modifying the anode target by removing a section of the top surface further comprises the step of forming a cut-out depth in the top surface, the cut-out depth having a concave configuration.

5. A method for reducing off-focal radiation in an X-ray tube, the method comprising the steps of:

providing an anode assembly;

providing a standard anode target associated with the anode assembly, the anode target having a top surface;

situating a detector along a line of sight of the top surface of the anode target;

generating x-rays in a focused electron beam, the x-rays being produced upon impact of the focused electron beam with the anode target, the focused electron beam also producing scatter of electrons that can cause off-focal radiation to be seen by the detector along the line of sight of the anode target top surface; and reducing the off-focal radiation seen by the detector by forming a cut-out depth in the anode target top surface to block the off-focal radiation from reaching the detector.

6. A method as claimed in claim 5 further comprising the step of notching the existing top surface of the anode target to form the cut-out depth.

7. A method as claimed in claim 5 wherein the step of reducing the off-focal radiation seen by the detector by forming a cut-out depth further comprises the step of forming a cut-out depth having squared edges.

8. A method as claimed in claim 5 further comprising the step of improving flatness of an umbra region of the electron beam.

9. A method as claimed in claim 5 wherein the step of reducing the off-focal radiation seen by the detector by forming a cut-out depth further comprises the step of forming the cut-out to have a depth sufficient to hide the line of sight of the top surface of the target from the detector.

10. A method as claimed in claim 5 wherein the anode target top surface emits off-focal radiation.

\* \* \* \* \*